(12) United States Patent
Reda et al.

(10) Patent No.: US 11,903,691 B2
(45) Date of Patent: Feb. 20, 2024

(54) COMBINED STEERING ENGINE AND LANDMARKING ENGINE FOR ELBOW AUTO ALIGN

(71) Applicant: Siemens Healthcare GmbH, Erlangen (DE)

(72) Inventors: Fitsum Aklilu Reda, West Chester, PA (US); Yiqiang Zhan, West Chester, PA (US); Martin Harder, Nuremberg (DE)

(73) Assignee: Siemens Healthineers AG, Forchheim (DE)

( * ) Notice: Subject to any disclaimer, the term of this patent is extended or adjusted under 35 U.S.C. 154(b) by 685 days.

(21) Appl. No.: 16/011,969

(22) Filed: Jun. 19, 2018

(65) Prior Publication Data

US 2019/0021625 A1   Jan. 24, 2019

Related U.S. Application Data

(60) Provisional application No. 62/533,874, filed on Jul. 18, 2017.

(51) Int. Cl.
*A61B 5/055* (2006.01)
*G01R 33/54* (2006.01)
(Continued)

(52) U.S. Cl.
CPC ............ *A61B 5/055* (2013.01); *A61B 5/4504* (2013.01); *A61B 5/4528* (2013.01); (Continued)

(58) Field of Classification Search
CPC ............... G01R 33/546; G01R 33/543; G01R 33/5608; A61B 5/055; A61B 5/417;
(Continued)

(56) References Cited

U.S. PATENT DOCUMENTS 8,190,232 B2   5/2012  Zhang et al.
2005/0154292 A1*  7/2005  Tank ................ A61B 6/545
                                                    600/410
(Continued)

FOREIGN PATENT DOCUMENTS

CN      1357132 A    7/2002
CN      1443513 A    9/2003
(Continued)

OTHER PUBLICATIONS

Steinbach, L. S., Fritz, R. C., Tirman, P. F., & Uffman, M. (1997). Magnetic resonance imaging of the elbow. European journal of radiology, 25(3), 223-241. (Year: 1997).*
(Continued)

*Primary Examiner* — Keith M Raymond
*Assistant Examiner* — Johnathan Maynard

(57) ABSTRACT

A method to automatically align magnetic resonance (MR) scans for diagnostic scan planning includes acquiring a three-dimensional (3D) localizer image of an anatomical object. One or more initial landmarks are identified in the 3D localizer image using a landmarking engine. One or more main axes associated with the anatomical object are identified based on the one or more initial landmarks. The 3D localizer image is registered to a canonical space based on the main axes associated to yield a registered 3D localizer image. The landmarking engine is applied to the registered 3D localizer image to yield one or more updated landmarks. A plurality of reference points for performing a MR scan are computed based on the one or more updated landmarks.

21 Claims, 6 Drawing Sheets

(51) Int. Cl.
*A61B 5/00* (2006.01)
*G06T 7/73* (2017.01)
(52) U.S. Cl.
CPC .............. *G01R 33/543* (2013.01); *G06T 7/73* (2017.01); *A61B 5/004* (2013.01); *A61B 5/0033* (2013.01); *G06T 2207/10088* (2013.01); *G06T 2207/30008* (2013.01)
(58) Field of Classification Search
CPC ... A61B 5/4504; A61B 5/4514; A61B 5/4528; A61B 6/466; A61B 6/5223; G09G 2360/145; G09G 3/3406; H05B 45/44; G06T 2207/10088; G06T 2207/20076; G06T 2207/20081; G06T 2207/20084; G06T 2207/30008; G06T 7/12; G06T 7/143
See application file for complete search history.

(56) References Cited

U.S. PATENT DOCUMENTS

| | | | | |
|---|---|---|---|---|
| 2008/0285829 | A1* | 11/2008 | Wang | A61B 5/055 382/131 |
| 2009/0080746 | A1* | 3/2009 | Xu | A61B 5/0037 382/131 |
| 2009/0093706 | A1* | 4/2009 | Zhang | A61B 5/417 382/128 |
| 2010/0121175 | A1* | 5/2010 | Jolly | A61B 5/055 600/410 |
| 2011/0282473 | A1* | 11/2011 | Pavlovskaia | G06T 7/13 700/98 |
| 2012/0093385 | A1* | 4/2012 | Yokosawa | A61B 5/055 382/131 |
| 2014/0093153 | A1* | 4/2014 | Sofka | G06T 7/0014 382/131 |
| 2014/0161334 | A1* | 6/2014 | Wang | G06T 7/149 382/131 |
| 2014/0364720 | A1* | 12/2014 | Darrow | G01R 33/543 600/410 |
| 2016/0157751 | A1* | 6/2016 | Mahfouz | A61B 6/12 600/409 |
| 2016/0260213 | A1* | 9/2016 | Reda | G06T 19/20 |
| 2017/0076453 | A1* | 3/2017 | Hu | G06T 7/0016 |
| 2018/0045800 | A1* | 2/2018 | Nielsen | G01R 33/546 |
| 2018/0360316 | A1* | 12/2018 | Kuo | A61B 6/463 |

FOREIGN PATENT DOCUMENTS

| | | |
|---|---|---|
| CN | 1745706 A | 3/2006 |
| CN | 101394790 A | 3/2009 |
| CN | 102203630 A | 9/2011 |

OTHER PUBLICATIONS

Elster, A. D. (2017). Performing an MR Scan. Retrieved from https://www.mriquestions.com/what-are-the-steps.html. (Year: 2017).*

Zhan, Y., Dewan, M., Harder, M., Krishnan, A., & Zhou, X. S. (2011). Robust automatic knee MR slice positioning through redundant and hierarchical anatomy detection. IEEE transactions on medical imaging, 30(12), 2087-2100. (Year: 2011).*

Zhan, Y., Dewan, M., Zhang, S., Peng, Z., Jian, B., & Zhou, X. S. (2016). From point to surface: Hierarchical parsing of human anatomy in medical images using machine learning technologies. In Machine Learning and Medical Imaging (pp. 383-410). Academic Press. (Year: 2016).*

* cited by examiner

COMBINED STEERING ENGINE AND LANDMARKING ENGINE FOR ELBOW AUTO ALIGN

This application claims the benefit of U.S. Provisional Application Ser. No. 62/533,874 filed Jul. 18, 2017, which is incorporated herein by reference in its entirety.

TECHNOLOGY FIELD

The present invention relates generally to methods, systems, and apparatuses for combining a steering engine and landmarking for Medical Resonance Imaging (MRI) applications that scan a subject's elbow. The techniques discussed herein may be applied, for example, to accurately and automatically align the elbow to aid in population-based study of the elbow anatomy within fast and automated planning of MRI examination or further image processing steps.

BACKGROUND

MRI is a noninvasive diagnostic technique that produces images of the body's soft tissue and bones based on magnetic resonance of atoms within the body. Typical applications of an MRI include imaging the brain, abdomen, and spine; however, in general, any anatomy containing soft tissue can be imaged with MRI. Of particular interest to the present disclosure, an MRI can be used to provide detailed diagnostic images of the human elbow.

There are various clinical scenarios where MRI images of the elbow can be used for diagnostic purposes. For example, an MRI offers an excellent tool that allows the clinician to identify the source of a patient's unexplained elbow pain, swelling, or atrophy. Similarly, when treating sports injuries such as tennis elbow, an MRI allows the clinician to directly view swelling of the tendons or other issues with the elbow. Additionally, an MRI can be used to track the progression of inflammatory diseases: arthritis or bursitis over time.

Figure 1A:
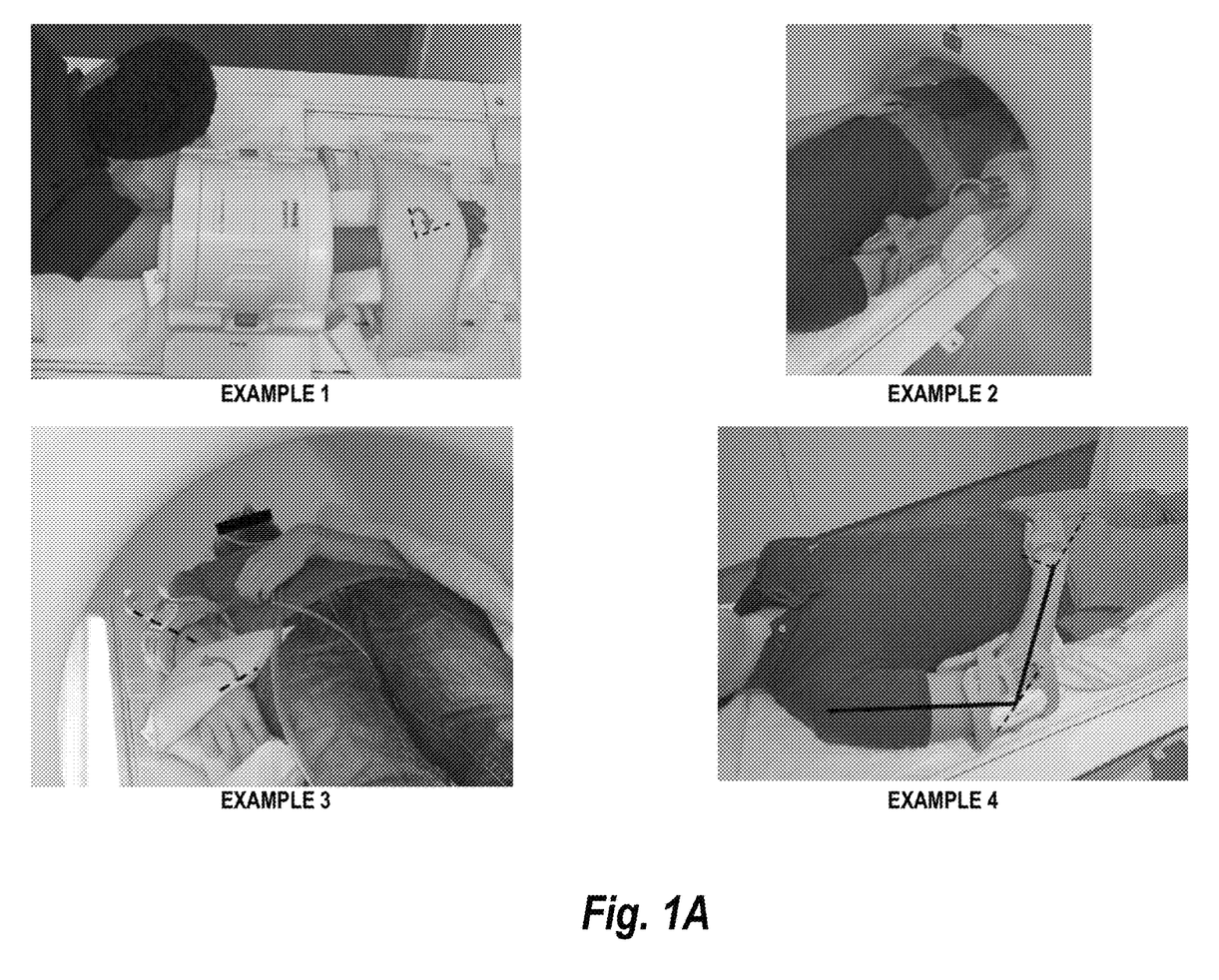
FIG. 1A illustrates how the positioning of the patient within the image acquisition device may vary based on the size of the patent.
Figure 1B:
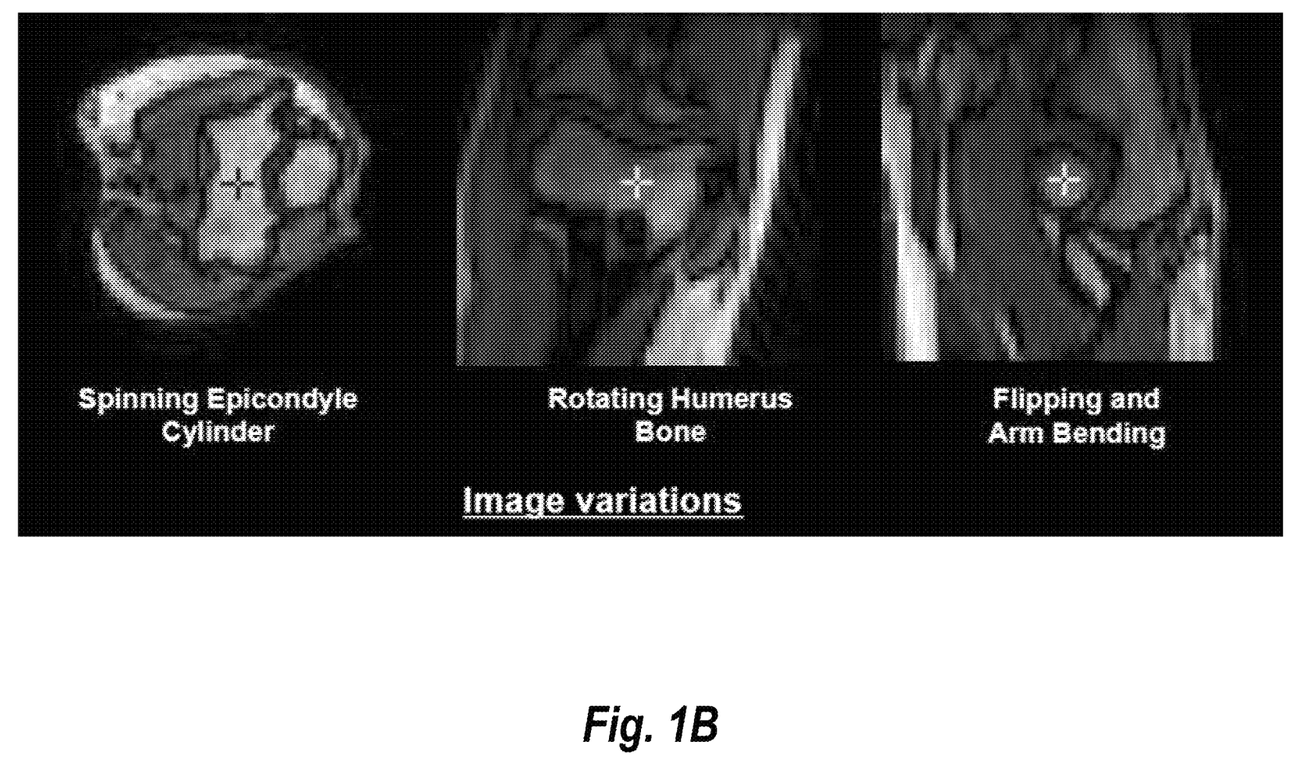
FIG. 1B shows the image variations that result from different arm positions within an MRI scanner.

Acquiring digital images of a human elbow can be especially challenging. As shown in FIG. 1A, the positioning of the patient within the image acquisition device may vary based on the size of the patent, as well as the bore size and field of view of the device itself. Moreover, the examples shown in FIG. 1A demonstrate that the elbow and hand may be positioned in the image acquisition device at different angulations due to injuries, blockades, etc. FIG. 1B shows the image variations that result from different arm positions within an MRI scanner.

The variations in positioning can also make certain MRI applications difficult to perform with accuracy. For example, the AutoAlign process used in Siemens MRI systems assist users in performing graphical slice positioning for MRI examinations. Part of the AutoAlign process involves the acquisition of orthogonal scouts of the anatomical area of interest. When the elbow is rotated or off-center from the field of view, acquiring scouts may require manual intervention by the operator. Using conventional techniques, the AutoAlign procedure requires 3-5 iterations of scout acquisition on average. Each iteration requires significant time. The whole procedure of multiple iterations usually takes several minutes in total and requires advanced anatomical and technical user experience. Thus, MRI elbow acquisitions usually take longer than the MRI acquisition of other joints (e.g., knee or hip). In turn, the MRI scanner cannot be utilized for other scanning applications.

Accordingly, for all the reasons set out above, it is desired to implement an alignment procedure specifically directed to elbow MRI applications that can be automated and eliminate the aforementioned deficiencies of conventional alignment solutions.

SUMMARY

Embodiments of the present invention address and overcome one or more of the above shortcomings and drawbacks, by providing methods, systems, and apparatuses related to performing an MRI scan of a subject's elbow using a steering engine and a landmarking engine.

According to some embodiments, a method to automatically align magnetic resonance (MR) scans for diagnostic scan planning includes acquiring a three-dimensional (3D) localizer image of an anatomical object. One or more initial landmarks are identified in the 3D localizer image using a landmarking engine. One or more main axes associated with the anatomical object are identified based on the one or more initial landmarks. The 3D localizer image is registered to a canonical space based on the main axes associated to yield a registered 3D localizer image. The landmarking engine is applied to the registered 3D localizer image to yield one or more updated landmarks. A plurality of reference points for performing an MR scan are computed based on the one or more updated landmarks.

In some embodiments of the aforementioned method, the anatomical object is an elbow and the initial landmarks are each located at the joint of the elbow. The initial landmarks may identify, for example, the medial collateral ligament, the lateral collateral ligament, or the annular ligament. The main axes are located along the humerus bone connected at the joint of the elbow, along the ulna bone connected at the joint of the elbow, along the radius bone connected at the joint of the elbow, or along the medial and lateral condyles of the elbow.

In some embodiments, the aforementioned method further includes obtaining a scan plan for the anatomical object based on the plurality of reference points. This scan plan for the anatomical object may be obtained by, for example, calculating a transformation matrix based on the plurality of reference points, and multiplying the transformation matrix by a standard slice package to yield the scan plan. The standard slice package may include a set of image slices with geometry descriptions to be acquired of the anatomical object in a standard coordinate system. In one embodiment, the method further includes executing the scan plan for the anatomical object using an imaging device using techniques generally known in the art of MRI systems.

According to another aspect of the present invention, article of manufacture for automatically aligning MR scans for diagnostic scan planning comprises a computer-readable, non-transitory medium holding computer-executable instructions for performing the method described above.

According to other embodiments, a system for automatically aligning MR scans for diagnostic scan planning comprises an MRI scanner configured to acquire a 3D localizer image of an anatomical object, and one or more computers. The computers identify (i) one or more initial landmarks in the 3D localizer image using a landmarking engine; and (ii) a main axis associated with the anatomical object based on the one or more initial landmarks. The computers register the 3D localizer image to a canonical space based on the main axis associated to yield a registered 3D localizer image, and apply the landmarking engine to the registered 3D localizer image to yield one or more updated landmarks.

Based on the updated landmarks, the computers compute a plurality of reference points for performing an MR scan. Using these reference points, the computers determine a scan plan and then execute that scan plan for the anatomical object using the MRI scanner.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF ILLUSTRATIVE EMBODIMENTS

The following disclosure describes the present invention according to several embodiments directed at methods, systems, and apparatuses related to the automatic alignment of anatomy within an image volume using a combination of a landmarking engine and a steering engine. Briefly, a rough localization of the center of an anatomical object is first performed using a landmarking engine. Then, the steering engine is used to detect two main axes of the elbow. Using the detected axes, the anatomical object is registered to a canonical space, before performing a fine detection of relevant anatomical features in the aligned image using the landmarking engine. Once all relevant landmarks are detected, they can be used to compute several reference boxes to scan the anatomical object in a desired orientation. The ability to accurately and automatically align the anatomical object could help in a population-based study of the object, or for fast planning of MR scanning, independent on the patients elbow pose on the table and independent on the patient pose registration data which often is related to the whole patient on the table but not related to the elbow itself.

Figure 2:
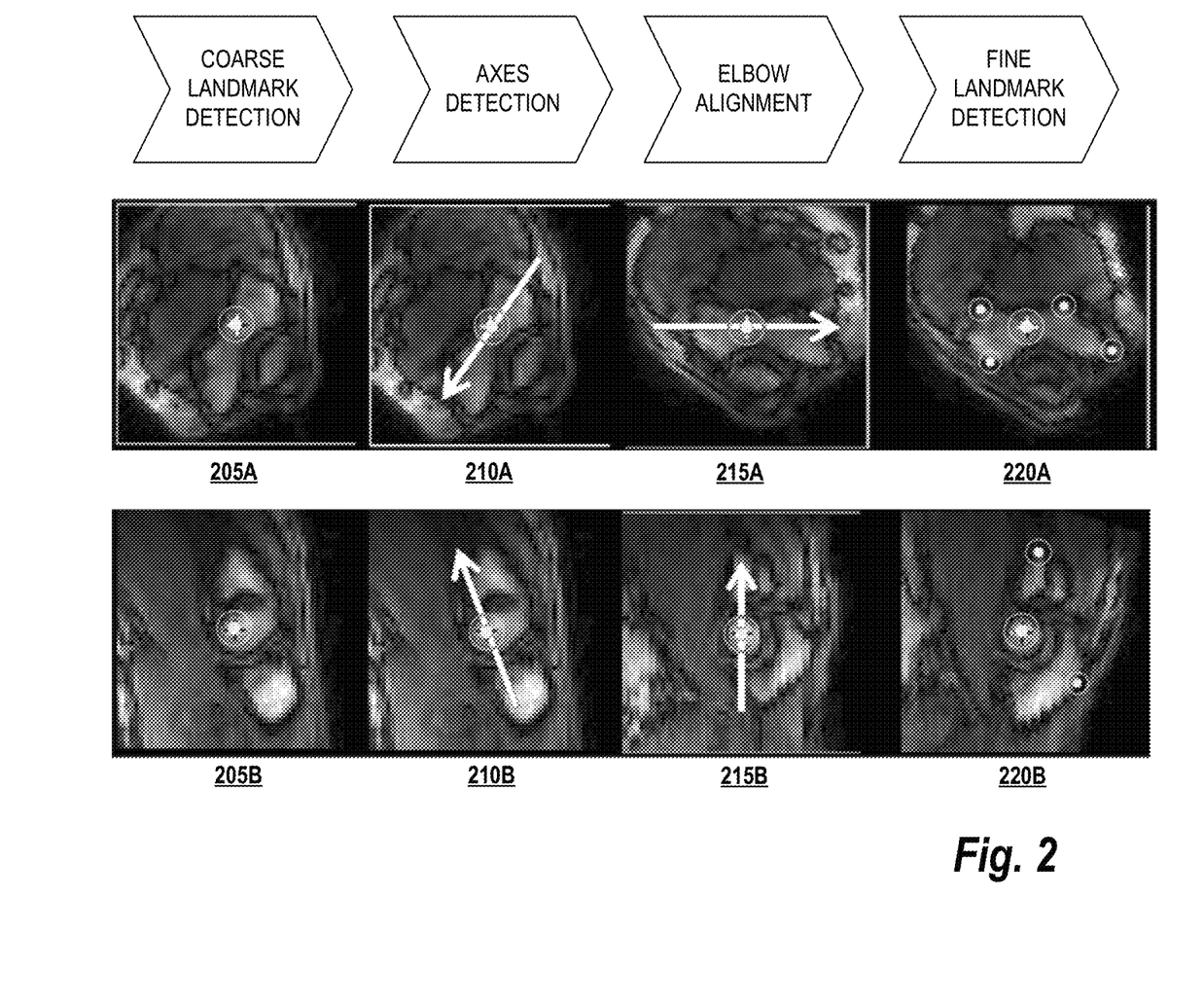
FIG. 2 provides a high-level overview of a framework for automatically aligning an anatomical object in an image volume, according to some embodiments.

FIG. 2 provides a high-level overview of a framework for automatically aligning an anatomical object in an image volume, according to some embodiments. The technology of the present application is described herein with reference to a human elbow; however it should be understood that the technology may be similarly applied to other anatomical objects that require alignment during image acquisition. Images are shown in FIG. 2 for each step of the framework to illustrate the step's processing of the input image volume.

Moving from left to right, the process generally entails first performing coarse landmark detection on an image volume using a landmarking engine. Image 205A and 205B show example output of executing the landmarking engine. In each case, a single landmark is identified at the joint of the elbow. During the next step in the framework, the steering engine is used to detect an axis through the landmark. Images 210A and 210B show result of axes detection with a single axis through the landmark presented in Images 205A and 205B. Next, the steering engine is used to align the image according to the detected axes. In the example Image 215A, the image is aligned such that the axis is in a horizontal direction; conversely in Image 215B, the axis is aligned in a vertical direction. Finally, at the final step of the framework, the landmarking engine is applied to the aligned image to perform fine landmark detection. As shown in Image 220A, the fine landmarking process results in 4 new landmarks. In Image 220B, 2 new landmarks are identified by the landmarking engine.

Figure 3:
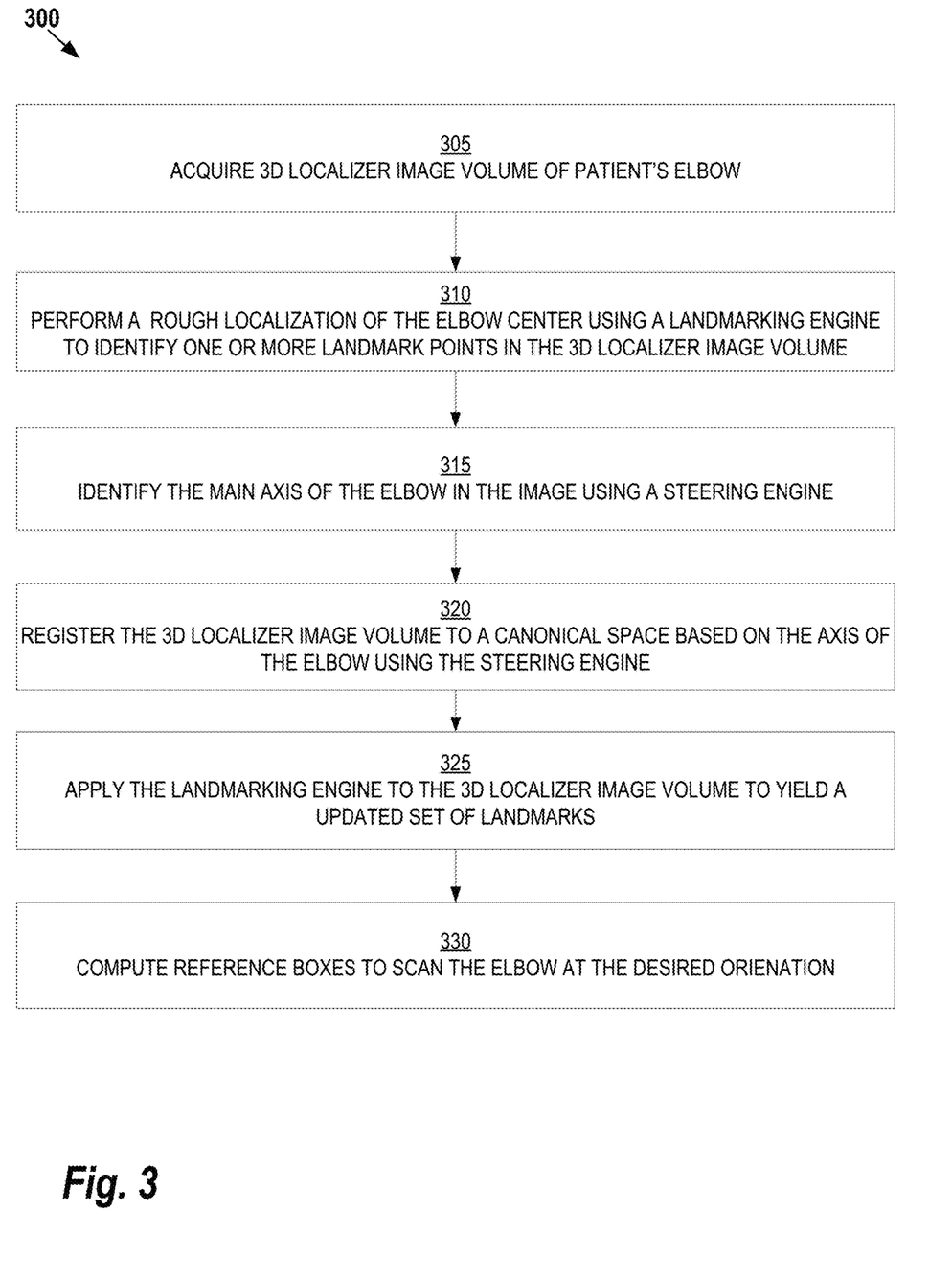
FIG. 3 provides a more detailed view of a method for automatically aligning an anatomical object in an image volume, according to some embodiments.

FIG. 3 provides a more detailed view of a method 300 for automatically aligning an anatomical object in an image volume, according to some embodiments. Starting at step 305, a scout scan of a patient's elbow is performed to acquire an almost isotropic 3D localizer image volume. As would be generally understood by one skilled in the art, a scout scan is a low-resolution volumetric image taken of a region of a patient. Typically, a scout scan (also referred to as a "localizer" scan) is setup in a way that the different tissue types of the anatomy (bones, muscles, fat, blood, etc.) are shown in the resulting images with a good brightness contrast. It is performed at the beginning of an MRI measurement session in order to define the scan's reference coordinate system with respect to the anatomy and the corresponding field-of-view (FOV) for subsequent acquisitions. It should be noted that, although a scout scan is discussed with reference to FIG. 3, in general the method 300 can be applied to image volumes acquired with any type of scanning.

Next at step 310, a rough localization of the elbow center is performed using a landmarking engine to identify one or more initial landmarks in the localizer image. The term "landmarking engine," as used herein refers to any combination of software and hardware that is able to automatically detect landmarks in a given image. For example, in some embodiments, the landmarking engine is the Automatic Landmarking and Parsing of Human Anatomy ("ALPHA") landmarking engine developed by Siemens Healthineers™. The ALPHA landmarking engine uses artificial intelligence, including a suite of machine learning based anatomical pattern recognition algorithms, to automatically detect landmarks and other structures in images. In other embodiments, different techniques that use discriminative learning and modeling of local appearance and shape may be employed. For example, discriminative techniques such as Boosting, AdaBoosting, Support Vector Machines and Decision Trees may be used for the modeling, detection, and localization of the landmarks. Additional examples of automatic landmarking may be found in U.S. Pat. No. 8,190,232 entitled "Automatic alignment of magnetic resonance imaging (MRI) brain scan by anatomic landmarks," the entirety of which is incorporated herein by reference.

The initial landmarks determined at step 310 generally identify a principal location of the anatomical object being scanned. Where the anatomical object is an elbow and the initial landmarks may each be located at the joint of the elbow. For example, the initial landmarks may identify the medial collateral ligament, the lateral collateral ligament, and/or the annular ligament at the elbow joint.

At step 315, one or more main axes of the elbow in the image is identified using a steering engine and the initial landmark(s). The term "steering engine," as used herein refers to software that automatically determines the orientation of anatomy in an image. Orientation in this context refers to one or more intrinsic directions of an anatomical structure. In the context of the elbow, these intrinsic directions may be, for example, the tangent directions at points along the humerus bone, the ulna bone, or the radius bone. In some embodiments, the orientation is determined using a classification algorithm. For example, in one embodiment, a classification model is trained to detect a desired orientation. This classification may employ, for example, marginal space learning (MSL) or a similar learning-based approach. Once trained, the classification may detect orientation in a new image based on the training data. In other embodiments, as an alternative to classification, regression-based methods may be used. For example, in one embodiment, a pre-trained regressor is applied to appearance features of the localizer image to predict a colatitude of the elbow. An optimal longitude corresponding to the predicted colatitude is then determined. This method is described in further detail in U.S. Pat. No. 9,704,300 entitled "Detection of anatomy orientation using learning-based regression," the entirety of which is incorporated herein by reference.

At step 320, the elbow is registered to a canonical space based on the medial-lateral condyle-axis of the elbow, the humerus shaft and the ulna axis. The canonical space in this context refers to a standard viewing position for the elbow. For example, in one embodiment, the canonical space is defined with the condyle axis as roughly the sagittal axis of the patient coordinate system and the humerus axis as roughly the transverse axis of the patient coordinate system. An operator may specify the canonical space directly as an input to the steering engine, but in the clinical praxis this input can be wrong, therefore it is not used. Preferably, a majority (or all) images used for training the landmarking engine is oriented in the same canonical space as used at step 315.

The exact technique employed for registration at step 320 may depend on the method used to determine the orientation of the axis at step 315. For example, where the regression-based method described above is employed the image volume may be re-oriented based on the predicted colatitude and the optimal longitude. The re-orientation may be performed a single time or, in some instances, it may be repeatedly performed to increase accuracy. For example, to continue with the example of the regression-based method, the re-orientation may be repeatedly performed until the predicted colatitude is less than a predetermined threshold (e.g., substantially close to zero). Note: the DICOM image position patient values may be ignored within this registration step as they often refer to the position of the patient within the device but not the position of the examined elbow; the elbow can be rotated or lifted up above the head in an arbitrary position.

Figure 4:
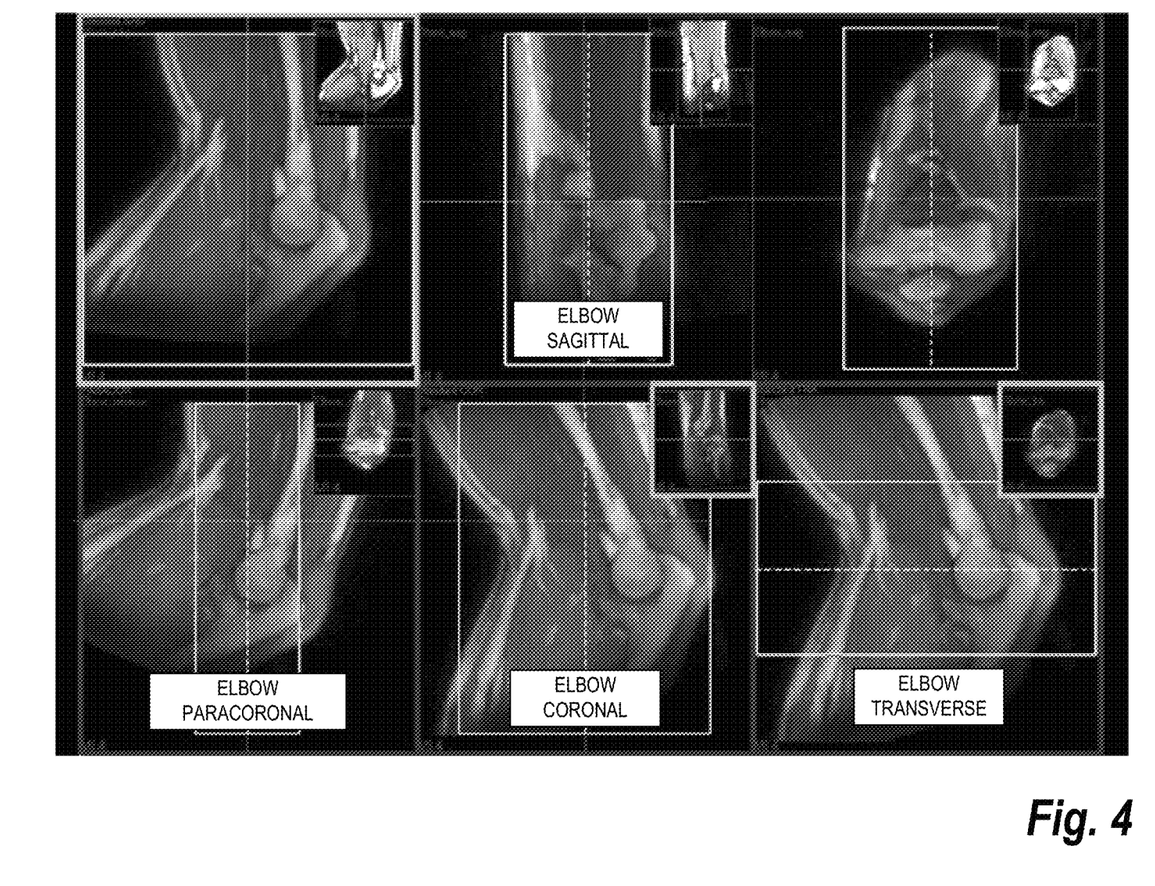
FIG. 4 illustrates a series of example reference boxes at various views that may be generated with the method described in FIG. 3.

Once the image is re-oriented, the landmarking engine is again applied to the image volume to yield an updated set of landmarks at step 325. Because the image has been reoriented into the canonical space, the landmarking engine provides more accurate results. Thus, the number of landmarks is greater than the landmarks determined at step 315. Once the landmarks are computed, they are used at step 330 to compute several reference points prescribing 3D bounding boxes to scan the elbow in a desired orientation. As is generally understood in the art, these reference points can be used by the MRI scanner to automate positioning and alignment of the anatomy-related sagittal, coronal and axial slices. FIG. 4 illustrates a series of example reference boxes at various views that may be generated with the method 300 described above. In some embodiments, these boxes are presented to the operator of the imaging device in a graphical user interface (GUI) for approval prior to executing a scan based on their reference points. If necessary, the operator may acquire another localizer image or apply additional offset parameters to the reference points and repeat the method 300 until the reference boxes produced by the method 300 are set as desired.

Once the reference points have been determined, they may be used to calculate a transformation matrix. The transformation matrix can be multiplied by a standard slice package to yield the scan plan. As is generally understood in the art, diagnostic scan planning is embodied by a slice package that comprises a set of slices (e.g., a stack of images) each having its own geometry description (e.g., center location, orientation, width and height). The slice package is a predefined slice package for a standard positioned patient and is generally available at most medical diagnostic centers. The standard positioned patient means that the patient is ideally positioned to be coincident with a standardized coordinate system. The origin of the standardized coordinate system is defined so that the center of the scan volume covers the elbow joint in the detected "clinical" orientations of the elbow (e.g., by a sagittal, coronal or transverse slice package). Thus, based on the determined points and bounding boxes the techniques described herein are able to cover the clinical region of interest with slice packages in different orientations. Once the scan plan has been generated, it can then be executed on an imaging device to acquire diagnostic images of the elbow.

Figure 5:
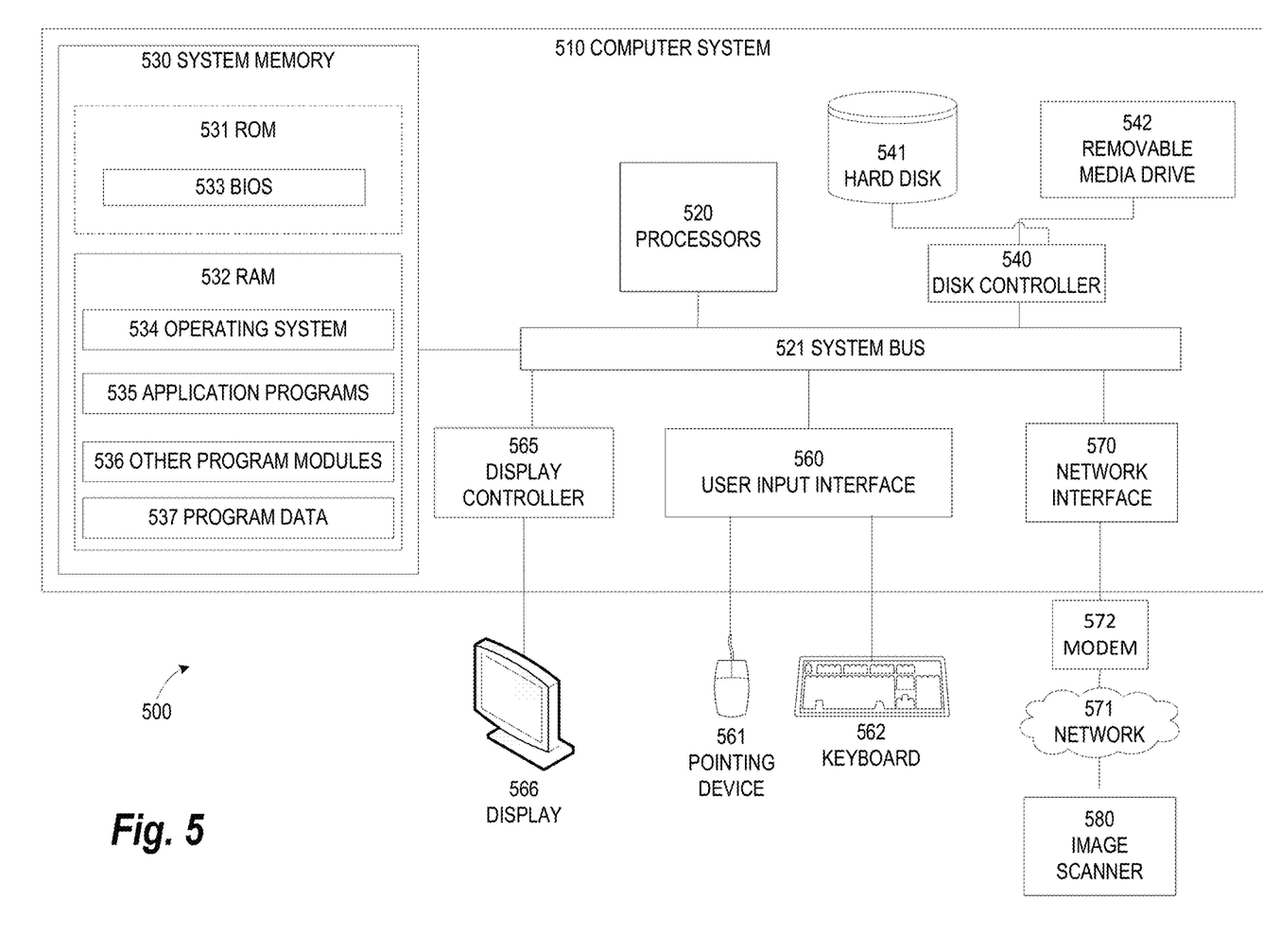
FIG. 5 illustrates an exemplary computing environment within which embodiments of the invention may be implemented.

FIG. 5 illustrates an exemplary computing environment 500 within which embodiments of the invention may be implemented. The computing environment 500 includes computer system 510, which is one example of a computing system upon which embodiments of the invention may be implemented. Computers and computing environments, such as computer system 510 and computing environment 500, are known to those of skill in the art and thus are described briefly herein.

As shown in FIG. 5, the computer system 510 may include a communication mechanism such as a bus 521 or other communication mechanism for communicating information within the computer system 510. The computer system 510 further includes one or more processors 520 coupled with the bus 521 for processing the information. The processors 520 may include one or more central processing units (CPUs), graphical processing units (GPUs), or any other processor known in the art.

The computer system 510 also includes a system memory 530 coupled to the bus 521 for storing information and instructions to be executed by processors 520. The system memory 530 may include computer readable storage media in the form of volatile and/or nonvolatile memory, such as read only memory (ROM) 531 and/or random access memory (RAM) 532. The system memory RAM 532 may include other dynamic storage device(s) (e.g., dynamic RAM, static RAM, and synchronous DRAM). The system memory ROM 531 may include other static storage device (s) (e.g., programmable ROM, erasable PROM, and electrically erasable PROM). In addition, the system memory 530 may be used for storing temporary variables or other intermediate information during the execution of instructions by the processors 520. A basic input/output system (BIOS) 533 contains the basic routines that help to transfer information between elements within computer system 510, such as during start-up, may be stored in ROM 531. RANI 532 may contain data and/or program modules that are immediately accessible to and/or presently being operated on by the processors 520. System memory 530 may additionally include, for example, operating system 534, application programs 535, other program modules 536 and program data 537. The application programs 535 may include, for example, the steering engine and landmarking engine (described above with reference to FIGS. 1 and 2) as well as an application which combines the two engines to perform the various methods described herein.

The computer system 510 also includes a disk controller 540 coupled to the bus 521 to control one or more storage devices for storing information and instructions, such as a hard disk 541 and a removable media drive 542 (e.g., floppy disk drive, compact disc drive, tape drive, and/or solid state drive). The storage devices may be added to the computer system 510 using an appropriate device interface (e.g., a small computer system interface (SCSI), integrated device electronics (IDE), Universal Serial Bus (USB), or FireWire).

The computer system 510 may also include a display controller 565 coupled to the bus 521 to control a display 566, such as a cathode ray tube (CRT) or liquid crystal display (LCD), for displaying information to a computer user. The computer system includes an input interface 560 and one or more input devices, such as a keyboard 562 and a pointing device 561, for interacting with a computer user and providing information to the processors 520. The pointing device 561, for example, may be a mouse, a trackball, or a pointing stick for communicating direction information and command selections to the processors 520 and for controlling cursor movement on the display 566. The display 566 may provide a touch screen interface which allows input to supplement or replace the communication of direction information and command selections by the pointing device 561.

The computer system 510 may perform a portion or all of the processing steps of embodiments of the invention in response to the processors 520 executing one or more sequences of one or more instructions contained in a memory, such as the system memory 530. Such instructions may be read into the system memory 530 from another computer readable medium, such as a hard disk 541 or a removable media drive 542. The hard disk 541 may contain one or more datastores and data files used by embodiments of the present invention. Datastore contents and data files may be encrypted to improve security. The processors 520 may also be employed in a multi-processing arrangement to execute the one or more sequences of instructions contained in system memory 530. In alternative embodiments, hardwired circuitry may be used in place of or in combination with software instructions. Thus, embodiments are not limited to any specific combination of hardware circuitry and software.

As stated above, the computer system 510 may include at least one computer readable medium or memory for holding instructions programmed according to embodiments of the invention and for containing data structures, tables, records, or other data described herein. The term "computer readable medium" as used herein refers to any medium that participates in providing instructions to the processor 520 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 541 or removable media drive 542. Non-limiting examples of volatile media include dynamic memory, such as system memory 530. Non-limiting examples of transmission media include coaxial cables, copper wire, and fiber optics, including the wires that make up the bus 521. Transmission media may also take the form of acoustic or light waves, such as those generated during radio wave and infrared data communications.

The computing environment 500 may further include the computer system 510 operating in a networked environment using logical connections to one or more image scanners such as imaging device 580. The imaging device 580 may be a radiology scanner such as a magnetic resonance (MR) scanner, PET/MR, X-ray or a CT scanner. When used in a networking environment, computer system 510 may include modem 572 for establishing communications with the imaging device 580 or a remote computing system over a network 571, such as the Internet. Modem 572 may be connected to bus 521 via user network interface 570, or via another appropriate mechanism. It should be noted that, although the imaging device 580 is illustrated as being connected to the computer system 510 over the network 571 in the example presented in FIG. 5, in other embodiments of the present invention, the computer system 510 may be directly connected to the image scanner 580. For example, in one embodiment the computer system 510 and the image scanner 580 are co-located in the same room or in adjacent rooms, and the devices are connected using any transmission media generally known in the art.

Network 571 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 510 and other computers (e.g., remote computer 580). The network 571 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 571.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

Unless stated otherwise as apparent from the following discussion, it will be appreciated that terms such as "segmenting," "generating," "registering," "determining," "aligning," "positioning," "processing," "computing," "selecting," "estimating," "detecting," "tracking", "covering" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

As used herein, the term "image" refers to multi-dimensional data composed of discrete image elements (e.g., pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. In general, the techniques described herein can be applied to images of any dimension, e.g., a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A "graphical user interface" (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112(f) the element is expressly recited using the phrase "means for."

We claim:

1. A method to automatically align magnetic resonance (MR) scans for diagnostic scan planning, comprising:
   acquiring a three-dimensional (3D) localizer image of an elbow;
   identifying one or more initial landmarks that include at least one ligament in the 3D localizer image using a landmarking engine;
   identifying one or more main axes associated with the elbow based on the one or more initial landmarks, the one or more main axes extending through the one or more initial landmarks;
   re-orienting the 3D localizer image to a standard viewing position of the elbow based on the identified one or more main axes and a condyle axis to yield a re-oriented 3D localizer image;
   applying the landmarking engine to the re-oriented 3D localizer image to yield one or more additional landmarks; and
   computing a plurality of reference points for performing an MR scan based on the one or more additional landmarks.

2. The method of claim 1, wherein the at least one ligament is a medial collateral ligament.

3. The method of claim 1, wherein the at least one ligament is a lateral collateral ligament.

4. The method of claim 1, wherein the at least one ligament is an annular ligament.

5. The method of claim 1, wherein at least one of the main axes is located along a humerus bone connected at a joint of the elbow.

6. The method of claim 1, wherein at least one of the main axes is located along an ulna bone connected at a joint of the elbow.

7. The method of claim 1, wherein at least one of the main axes is located along a radius bone connected at a joint of the elbow.

8. The method of claim 1, wherein at least one of the main axes is located along medial and lateral condyles of the elbow.

9. The method of claim 1, wherein a steering engine is used to automatically (a) identify the main axis associated with the elbow and (b) re-orient the 3D localizer image to yield a re-oriented 3D localizer image based on the main axis.

10. The method of claim 1, further comprising:
obtaining a scan plan for the elbow based on the plurality of reference points.

11. The method of claim 10, wherein the scan plan for the elbow is obtained by:
calculating a transformation matrix based on the plurality of reference points, and
multiplying the transformation matrix by a standard slice package to yield the scan plan.

12. The method of claim 11, wherein the standard slice package comprises a set of image slices with geometry descriptions to be acquired of the elbow in a standard coordinate system.

13. The method of claim 12, further comprising:
executing the scan plan for the elbow using an imaging device.

14. An article of manufacture for automatically aligning MR scans for diagnostic scan planning, the article of manufacture comprising a computer-readable, non-transitory medium holding computer-executable instructions for performing a method comprising:
identifying one or more initial landmarks that include at least one ligament in a 3D localizer image of an elbow using a landmarking engine;
identifying a main axis associated with the elbow based on the one or more initial landmarks, the main axis extending through the one or more initial landmarks;
re-orienting the 3D localizer image to a standard viewing position of the elbow based on the main axis to yield a re-oriented 3D localizer image;
applying the landmarking engine to the re-oriented 3D localizer image to yield one or more updated landmarks; and
computing a plurality of reference points for performing an MR scan based on the one or more updated landmarks.

15. The article of manufacture of claim 14, wherein the article of manufacture uses a steering engine to automatically (a) identify the main axis associated with the elbow and (b) rotate the 3D localizer image to yield a rotated 3D localizer image based on the main axis.

16. The article of manufacture of claim 14, wherein the method further comprises:
obtaining a scan plan for the elbow based on the plurality of reference points.

17. The article of manufacture of claim 16, wherein the scan plan for the elbow is obtained by:
calculating a transformation matrix based on the plurality of reference points, and multiplying the transformation matrix by a standard slice package to yield the scan plan.

18. The article of manufacture of claim 17, wherein the standard slice package comprises a set of image slices with geometry descriptions to be acquired of the elbow in a standard coordinate system.

19. The article of manufacture of claim 18, wherein the method further comprises:
executing the scan plan for the elbow using an imaging device.

20. A system for automatically aligning MR scans for diagnostic scan planning, the system comprising:
an MRI scanner configured to acquire a 3D localizer image of an elbow and one or more computers configured to:
identify one or more initial landmarks that include at least one ligament in the 3D localizer image using a landmarking engine;
identify a main axis associated with the elbow based on the one or more initial landmarks, the main axis extending through the one or more initial landmarks;
re-orient the 3D localizer image to yield a re-oriented 3D localizer image based on the main axis, wherein the re-oriented 3D localizer image corresponds with a standard viewing position of the elbow;
apply the landmarking engine to the re-oriented 3D localizer image to yield one or more updated landmarks;
compute a plurality of reference points for performing a MR scan based on the one or more updated landmarks;
determine a scan plan based on the plurality of reference points; and
execute the scan plan for the elbow using the MRI scanner.

21. The method of claim 1, wherein the one or more initial landmarks are located at a joint of the elbow and locate a center of the elbow.

* * * * *